United States Patent [19]

De Simone

[11] Patent Number: 5,108,993

[45] Date of Patent: Apr. 28, 1992

[54] PHARMACEUTICAL COMPOSITION COMPRISING ZIDOVUDINE AND INOSIPLEX OR COMPONENTS THEREOF FOR THE TREATMENT OF AIDS-RELATED SYNDROMES

[75] Inventor: Claudio De Simone, Rome, Italy

[73] Assignee: Sigma-Tau Industrie Farmaceutiche Riunite S.p.A., Rome, Italy

[21] Appl. No.: 595,758

[22] Filed: Oct. 9, 1990

Related U.S. Application Data

[63] Continuation of Ser. No. 412,471, Sep. 26, 1989, abandoned.

[30] Foreign Application Priority Data

| Sep. 28, 1988 | [IT] | Italy | 48338 A88 |
| Oct. 12, 1988 | [IT] | Italy | 48444 A88 |
| Oct. 12, 1988 | [IT] | Italy | 48445 A88 |

[51] Int. Cl.$^5$ .................. A61K 31/70; A61K 31/66
[52] U.S. Cl. ................................ 514/50; 514/45; 514/114; 514/563; 514/667; 514/922
[58] Field of Search ............ 514/50, 45, 114, 166, 514/663, 563, 667

[56] References Cited

U.S. PATENT DOCUMENTS 4,866,035  9/1989  Durette .................... 514/8

FOREIGN PATENT DOCUMENTS 2181128  4/1987  United Kingdom.

OTHER PUBLICATIONS

Langtry et al., *Drugs*, vol. 37, pp. 408-450 (1989).
Strategies for antiviral therapy in AIDS, Mitsuya et al. Nature 325, 773 (1987).
Synergistic cytotoxic effect of AZT and recombinant interferon alpha on normal human bone marrow progenitor cells, Berman et al. Blood 74, 1281 (1989).
AIDS treatment news Apr. 1986-1989. p. 158.
Antiviral therapy in AIDS, Sandstrom et al., Drugs 34, 372 (1987) The toxicity of AZT in treatment of patients with AIDS and AIDS related complex Richman et al. New Engl. J. of Med. Jul. 23, 1987, p. 192.

*Primary Examiner*—Thurman K. Page
*Assistant Examiner*—G. S. Kishore
*Attorney, Agent, or Firm*—Oblon, Spivak, McClelland, Maier & Neustadt

[57] ABSTRACT

The administration of a pharmaceutical mixture consisting of the immunomodulator inosiplex or components thereof (p-acetamidobenzoic acid and inosine), and zidovudine (3'-azio-3'-deoxythymidine, AZT) makes it possible to remarkably increase the basal plasma levels and the plasma half-life of AZT in a patient suffering from AIDS. This permits lowering the dose of AZT administered daily (1,200 mg per diem), thus achieving an attendant decrease in the serious toxicity of AZT while maintaining AZT's therapeutic efficacy. The lower toxicity of the mixture compared with AZT alone now justifies AZT administration to asymptomatic HIV-seropositive patients to whom its administration to dated was deemed inadvisable because of AZT's serious toxicity.

5 Claims, No Drawings

PHARMACEUTICAL COMPOSITION COMPRISING ZIDOVUDINE AND INOSIPLEX OR COMPONENTS THEREOF FOR THE TREATMENT OF AIDS-RELATED SYNDROMES

This application is a continuation of application Ser. No. 07/412,471, filed on Sep. 26, 1989, now abandoned.

BACKGROUND OF THE INVENTION

1. Field of the Invention

The present invention relates to a pharmaceutical composition containing inosiplex or inosiplex components (as will be illustrated in detail hereinbelow) and zidovudine for treating patients suffering from AIDS and AIDS-related syndromes and asymptomatic HIV-seropositive patients. By "AIDS-related syndromes", ARC (AIDS-related complex), LAS (lymphadenopathy syndrome) and Kaposi's sarcoma are meant.

2. Discussion of the Background

Zidovudine (3'-azido-3'-deoxythymidine,AZT), a thymidine analog, is at present the only registered somewhat effective drug for the treatment of AIDS and AIDS-related syndromes. AZT is an inhibitor of the in vitro replication of some retroviruses, including HIV (Human Immunodeficiency Virus), AIDS etiological agent. Cellular thymidine kinase converts zidovudine into zidovudine monophosphate. This compound is finally converted into the triphosphate derivative which interferes with the RNA-dependent DNA-polymerase (viral reverse transcriptase), thus inhibiting viral replication. In fact, in vitro zidovudine triphosphate is incorporated into the DNA growing chains by viral reverse transcriptase, whereby DNA chain is terminated.

For a suitable and therapeutical significant plasma level to be warranted, the recommended AZT dose is 200 mg every 4 hours around the clock, even though this may interrupt the patient's normal sleep schedule.

This demanding dosing schedule is brought about by the short half-life (it averages about 1 hour) of the drug which is rapidly inactivated via glucuronidation in the liver.

Unfortunately, at the therapeutically effective doses AZT brings about severe side-effects including anemia which requires frequent blood transfusions, leukopoenia and bone marrow toxicity. Frequently, these side-effects have been severe enough to require dosage modification or even discontinuance of the drug administration. A lowered drug dose leads, however, to therapeutical unsuitable AZT plasma levels.

AZT toxicity has to date made it inadvisable to administer the drug to asymptomatic HIV-seropositive patients.

The toxicity problem of AZT is further worsened because clinical practice seems to confirm that, once the treatment with AZT is started, it must last for long time periods if not for the entire life-span of the patient.

With a view to prolonging AZT half-life and enhancing its antiretroviral effect, in any case aiming at lowering the daily dose while maintaining its therapeutical advantages, some associations of zidovudine with other drugs, some antiviral and some having different therapeutical ends, have been proposed already. Recently, 800 mg acyclovir and 100 mg AZT (one half of the recommended dose) every 4-6 hours have been reported to act synergistically against the virus. However, neurotoxicity (with profound drowsiness and lethargy) which recurred on rechallenge and resolved following discontinuance of acyclovir, has been reported (see Drug Information 88, page 396).

In the U.K. patent application GB 2 181 128 A published Apr. 15, 1987, there is disclosed the synergistic effect on zidovudine of the following drugs: alpha-, beta-, and gamma-interferons, dilazep, dipyridamole, papaverine, mioflazine, hexobendine, lidoflazine, probenecid, acyclovir, interleukine II, suramine, foscarnet, HPA-23, levamisole, dideoxynucleosides (e.g. dideoxycytidine and dideoxyadenosine) and thymosine.

At any rate, the pharmacokinetics of AZT is not significantly affected by the concomitant administration of the above-identified drugs.

It, therefore, follows that the overall antiviral effect of the formulation is the sum of the effects of the two drugs, only one of them, however, (i.e. AZT) exhibiting a certain efficacy against HIV. Also the side-effects of the formulation are the sum of those of the two drugs, unless their doses are decreased. However, since—as indicated above—the only anti-HIV drug is AZT, it still remains to be proven whether the synergism between AZT and the associated drug against HIV compensates for the lower AZT dose in the formulation.

SUMMARY OF THE INVENTION

It has now been found that it is possible to maintain in patients suffering from AIDS and AIDS-related syndromes and in asymptomatic HIV-seropositive patients who are administered no more than 600 mg zidovudine/day (i.e. no more than one-half of the dose at present reccommended) therapeutically effective plasma levels of zidovudine (i.e. comprised between about 0.45 and 2.25 micromoles/ml) whithout any toxic and side-effects taking place, provided that these patients are orally or parenterally administered a composition comprising (a) zidovudine
(b) inosiplex, or
(b') p-acetamidobenzoic acid, or
(b") p-acetamidobenzoic acid and inosine.

Inosiplex (isoprinosine, methysoprinol) is inosine: dimethylaminoisopropanoletamidobenzoate (1:3). Inosiplex is a well-known antiviral immunomodulator.

DETAILED DESCRIPTION OF THE PREFERRED EMBODIMENTS

In the composition (a)+(b), the weight ratio zidovudine:inosiplex is comprised between about 1:8 and 1:16.

In the composition (a)+(b'), the weight ratio zidovudine:p-acetamidobenzoic acid is comprised between about 1:10 and 1:100.

In the composition (a)+(b"), the weight ratio zidovudine:inosine:p-acetamidobenzoic acid is comprised between about 1:5:5 and 1:50:50.

For instance, compositions in unit dosage form comprise, for about 100 milligrams zidovudine, about 1 gram inosiplex, or about 1 gram of p-acetamidobenzoic acid, or about 1 gram inosine and 1 gram p-acetamidobenzoic acid.

The preferred therapeutical dosing regimen for treating these patients according to the present invention comprises the substantially concomitant oral or parenteral administration, about every 6 hours, of 1.5-2 mg zidovudine/kg body weight and about 15-20 mg inosiplex/kg body weight or about 1.5-2 mg zidovudine/kg body weight and about 15-20 mg p-acetamidobenzoic acid/kg body weight or about 1.5-2 mg zidovudine/kg body weight and about 15-20 mg inosine/kg body weight and about 15-20 mg p-acetamidobenzoic acid/kg body weight.

Some clinical studies are illustrated hereinbelow, which show the efficacy of the zidovudine/inosiplex (or components thereof) composition according to the present invention.

Clinical Study 1: Composition (a)+(b)

The study was carried out on 5 AIDS patients (Group IV, subgroup C, CDC (Center for Disease Control), staging criteria, Classification system for Human T-lymphotropic virus type III lymphadenopathy associated virus infections. MM WR 1986, 35:334-39) who had developped bone marrow toxicity on 200 mg AZT orally every four hours (1,200 mg total daily dose) and again, when maintained for 2 months on a lower dose of 800 mg daily. They were subsequently placed on a dose of 100 mg AZT every 6 hours (400 mg total daily dose). However, pharmacokinetics studies showed that at this dose the plasma levels were below the therapeutical threshold.

The patients were then placed on the following dosing regimen:

AZT (100 mg every 6 hrs; one third of the presently recommended dosage) was administered orally to the 5 AIDS patients for 7 days, followed by 100 mg AZT and 1 gm inosiplex (INPX) every 6 hrs for an additional 7 days. The patients ranged in weight from 52.6 kg to 63.2 kg; these doses thus represented 1.58 to 1.98 mg/kg body weight of AZT and 15.8 to 19 mg/kg of INPX. No other drugs that are believed to affect hepatic glucuronidation were administered.

On day 7, while the patients were receiving AZT alone and on day 14 while they were receiving both AZT and INPX, blood samples were obtained every hour over a 6-hour dosing interval for measurement of AZT concentration by a specific AZT radioimmunoassay (RIA; ZDVTRAC, Incstar, U.S.A.)

On day 7, when patients were receiving 100 mg of AZT every 6 hours but not INPX, pharmacokinetics analysis showed that the mean peak plasma level of AZT (the mean of the highest level for each individual) was 1.47 $\mu$M (standard deviation 0.75 $\mu$M, range, 0.06 to 2.52 $\mu$M) and the mean nadir level was 0.24 $\mu$M (standard deviation 0.19 $\mu$M, range, 0.06 to 0.5 $\mu$M). Subsequent pharmacokinetic analysis of AZT levels done on day 14th when the same patients were also receiving INPX, showed that the mean peak plasma level of AZT was 2.25 $\mu$M (standard deviation 1.5 $\mu$M, range, 0.14 to 4.4 $\mu$M) and the mean nadir level was 0.46 $\mu$M (standard deviation 0.25 $\mu$M, range, 0.15 to 0.84 $\mu$M).

At time 0, before the taking of AZT alone or of AZT and INPX, the AZT serum levels always resulted higher in the patients receiving both drugs than in those taking AZT alone (0.18 $\mu$M versus 0.013 $\mu$M). The statistical analysis of the area under the serum concentration-time curve resulted significantly increased ($p<0.01$) in patients taking AZT and INPX. Serum half-life of the elimination phase ($T\frac{1}{2}$) was significantly shorter ($p<0.01$) for AZT (44 min) in comparison with that of AZT+INPX (70 min).

Clinical Study No. 2: Composition (a)+(b')

Patients, treatment with AZT alone and results of pharmacokinetic studies as in the clinical study 1.

The patients were then placed on the following dosing regimen:

AZT (100 mg every 6 hrs; one third of the presently recommended dosage) was administered orally to the 5 AIDS patients for 7 days, followed by 100 mg AZT and 1 gm p-acetamidobenzoic acid every 6 hrs for an additional 7 days. The patients ranged in weight from 52.6 kg to 63.2 kg; these doses thus represented 1.58 to 1.98 mg/kg body weight of AZT and 15.8 to 19 mg/kg of p-acetamidobenzoic acid. No other drugs that are believed to affect hepatic glucuronidation were administered.

On day 7, while the patients were receiving AZT alone and on day 14 while they were receiving both AZT and p-acetamidobenzoic acid, blood samples were obtained every hour over a 6-hour dosing interval for measurement of AZT concentration by specific AZT radioimmunoassay (RIA; ZDVTRAC, Incstar, U.S.A.).

On day 7, when patients were receiving 100 mg of AZT every 6 hours but not p-acetamidobenzoic acid, pharmacokinetic analysis showed that the mean peak plasma level of AZT (the mean of the highest level for each individual) was 1.52 $\mu$M (standard deviation 0.75 $\mu$M, range, 0.04 to 2.46 $\mu$M) and the mean nadir level was 0.25 $\mu$M (standard deviation 0.19 $\mu$M, range, 0.04 to 0.6 $\mu$M). Subsequent pharmacokinetic analysis of AZT levels done on day 14th when the same patients were also receiving p-acetamidobenzoic acid, showed that the mean peak plasma level of AZT was 2.45 $\mu$M (standard deviation 1.8 $\mu$M, range, 0.16 to 4.7 $\mu$M) and the mean nadir level was 0.49 $\mu$M (standard deviation 0.28 $\mu$M, range 0.14 to 0.88 $\mu$M).

At time 0, before the taking of AZT alone or of AZT and p-acetamidobenzoic acid, the serum level always resulted higher in the patients receiving both drugs that in those taking AZT alone (0.16 $\mu$M versus 0.010 $\mu$M). The statistical analysis of the area under the serum concentration-time curve resulted significantly increased ($p<0.01$) in patients taking AZT and p-acetamidobenzoic acid.

Clinical Study 3: Composition (a)+(b'')

Patients, treatment with AZT alone and results of the pharmacokinetic studies as in the clinical study 1.

The patients were then placed on the following dosing regimen:

AZT (100 mg every 6 hrs; one third of the presently recommended dosage) was administered orally to the 5 AIDS patients for 7 days, followed by 100 mg AZT and 1 gm inosine and 1 gm INPX every 6 hrs for an additional 7 days. The patients ranged in weight from 52.6 kg to 63.2 kg; these doses thus represented 1.58 to 1.98 mg/kg body weight of AZT and 15.8 to 19 mg/kg of inosine and INPX. No other drugs that are believed to affect hepatic glucuronidation were administered.

On day 7, while the patients were receiving AZT alone and on day 14 while they were receiving both AZT, inosine and INPX, blood samples were obtained every hour over a 6-hour dosing interval for measurement of AZT concentration by a specific AZT radioimmunoassay (RIA; ZDVTRAC, Incstar, U.S.A.).

On day 7, when patients were receiving 100 mg of AZT alone every 6 hours, pharmacokinetic analysis showed that the mean peak plasma level of AZT (the mean of the highest level for each individual) was 1.41 $\mu$M (standard deviation 0.70 $\mu$M, range, 0.03 to 2.16 $\mu$M) and the mean nadir level was 0.21 $\mu$M (standard deviation 0.16 μM, range, 0.06 to 0.8 μM). Subsequent pharmacokinetic analysis of AZT levels done on day 14th when the same patients were also receiving inosine and INPX, showed that the mean peak plasma level of AZT was 2.76 μM (standard deviation 1.3 μM, range, 0.15 to 4.2 μM) and the mean nadir level was 0.51 μM (standard deviation 0.26 μM, range, 0.11 to 0.82 μM).

At time 0, before the taking of AZT alone or of AZT, inosine and INPX, the AZT serum levels always resulted higher in the patients receiving both drugs that in those taking AZT alone (0.22 μM versus 0.016 μM). The statistical analysis of the area under the serum concentration-time curve resulted significantly increased ($p<0.01$) in patients taking AZT, inosine and INPX.

What is claimed is:

1. An orally or parenterally administrable zidovudine-containing pharmaceutical composition for treating patients suffering from AIDS and AIDS-related syndromes as well as asymptomatic HIV-seropositive patients, characterized in that it comprises
   (a) zidovudine and an amount of one member selected from the group consisting of
   (b) inosiplex,
   (b') p-acetamidobenzoic acid, and
   (b") p-acetamidobenzoic acid and inosine effective for maintaining in such patients a zidovudine plasma level above the therapeutic threshold, the amount of zidovudine being ineffective for bringing about the onset of zidovudine toxic- and side-effects, wherein the weight ratio of zidovudine to inosiplex is 1:8 to 1:16, the weight ratio of zidovudine to p-acetamidobenzoic acid is 1:10 to 1:100, and the weight ratio of zidovudine to inosine to p-acetamidobenzoic acid is 1:5:5 to 1:50:50.

2. The composition of claim 1 in unit dosage form containing about 100 milligrams zidovudine and about 1 gram inosiplex.

3. The composition of claim 1 in unit dosage form containing about 100 milligram of zidovudine and about 1 gram of p-acetamidobenzoic acid.

4. The composition of claim 1 in unit dosage form containing about 100 milligrams of zidovudine and about 1 gram inosine and 1 gram p-acetamidobenzoic acid.

5. A method for maintaining zidovudine plasma levels comprised between about 0.45 and 2.25 micromoles/ml in patients suffering from AIDS or AIDS-related syndromes and in asymptomatic HIV-seropositive patients who are administered no more than 600 mg zidovudine/day which comprises contemporaneously administering, along with zidovudine, inosiplex at a zidovudine/inosiplex weight ratio comprised between about 1:8 and 1:16; or p-acetamidobenzoic acid, at a zidovudine/p-acetamidobenzoic acid comprised 1:10 and 1:100; or inosine/p-acetamidobenzoic acid, at a zidovudine/inosine/p-acetamidobenzoic acid comprised between about 1:5:5 and 1:50:50.

* * * * *